United States Patent
Falevsky et al.

(12) 
(10) Patent No.: US 10,888,271 B2
(45) Date of Patent: Jan. 12, 2021

(54) SYSTEMS, APPARATUS AND METHODS FOR USING BIOFEEDBACK TO FACILITATE A DISCUSSION

(71) Applicant: Louise M. Falevsky, Rolling Hills Estates, CA (US)

(72) Inventors: Louise M. Falevsky, Rolling Hills Estates, CA (US); Robert D. Fish, Tustin, CA (US)

(73) Assignee: Louise M. Falevsky, Rolling Hills Estates, CA (US)

(*) Notice: Subject to any disclaimer, the term of this patent is extended or adjusted under 35 U.S.C. 154(b) by 36 days.

(21) Appl. No.: 15/939,032

(22) Filed: Mar. 28, 2018

(65) Prior Publication Data
US 2018/0214075 A1  Aug. 2, 2018

Related U.S. Application Data

(63) Continuation-in-part of application No. 15/530,169, filed on Dec. 8, 2016, now Pat. No. 9,953,650.

(51) Int. Cl.
| | | |
|---|---|---|
| *G10L 15/22* | (2006.01) |
| *A61B 5/00* | (2006.01) |
| *A61B 5/16* | (2006.01) |
| *G16H 10/60* | (2018.01) |
| *G16H 10/20* | (2018.01) |
| *G16H 20/70* | (2018.01) |
| *G16H 50/30* | (2018.01) |
| *G10L 15/08* | (2006.01) |
| *A61B 5/053* | (2006.01) |
| *A61B 5/08* | (2006.01) |
| *A61B 5/0476* | (2006.01) |
| *A61B 5/024* | (2006.01) |
| *G10L 25/66* | (2013.01) |

(52) U.S. Cl.
CPC ............... *A61B 5/486* (2013.01); *A61B 5/16* (2013.01); *G10L 15/22* (2013.01); *G16H 10/20* (2018.01); *G16H 10/60* (2018.01); *G16H 20/70* (2018.01); *G16H 50/30* (2018.01); *A61B 5/024* (2013.01); *A61B 5/0476* (2013.01); *A61B 5/0533* (2013.01); *A61B 5/0816* (2013.01); *A61B 5/163* (2017.08); *A61B 5/7465* (2013.01); *G10L 25/66* (2013.01); *G10L 2015/088* (2013.01); *G10L 2015/225* (2013.01); *G10L 2015/227* (2013.01)

(58) Field of Classification Search
CPC .......................................................... G01L 15/22
See application file for complete search history.

(56) References Cited

U.S. PATENT DOCUMENTS

| | | | | |
|---|---|---|---|---|
| 5,562,453 A | * | 10/1996 | Wen ................. | G10L 15/22 434/156 |
| 5,647,834 A | * | 7/1997 | Ron ................. | A61B 5/16 600/23 |

(Continued)

*Primary Examiner* — Jialong He
(74) *Attorney, Agent, or Firm* — Fish IP Law, LLP

(57) ABSTRACT

Computer implemented biofeedback is used to facilitate discussions. Preferred embodiments include the steps of identifying a concept used by at least one of the participants during a discussion, sourcing additional content from outside the discussion, detecting use of a trigger expression by one of the participants, and then further to detecting use of the trigger expression rendering at least some of the additional content to one or more of the participants as an electronic biofeedback signal.

15 Claims, 3 Drawing Sheets

(56) References Cited

U.S. PATENT DOCUMENTS

| | | | |
|---|---|---|---|
| 5,722,418 A | 3/1998 | Bro | |
| 5,794,203 A * | 8/1998 | Kehoe | A61F 5/58 704/271 |
| 6,001,065 A | 12/1999 | DeVito | |
| 6,151,571 A | 11/2000 | Pertrushin | |
| 6,255,937 B1 | 7/2001 | Hamaguchi | |
| 6,425,764 B1 | 7/2002 | Lamson | |
| 6,450,820 B1 | 9/2002 | Palsson et al. | |
| 6,728,680 B1 | 4/2004 | Aaron et al. | |
| 7,805,486 B2 * | 9/2010 | Hering | H04Q 11/04 709/204 |
| 7,904,510 B2 * | 3/2011 | Anderson | G06F 17/24 707/662 |
| 7,933,226 B2 | 4/2011 | Woodruff et al. | |
| 8,062,129 B2 | 11/2011 | Pope et al. | |
| 8,131,750 B2 | 3/2012 | Bathiche et al. | |
| 8,458,193 B1 * | 6/2013 | Procopio | G06F 16/313 707/749 |
| 8,670,018 B2 * | 3/2014 | Cunnington | G06Q 10/10 348/14.08 |
| 9,173,567 B2 | 11/2015 | Jain et al. | |
| 9,292,858 B2 | 3/2016 | Marci et al. | |
| 9,324,096 B2 | 4/2016 | Higgins | |
| 9,374,394 B2 | 6/2016 | Kahn | |
| 2002/0010587 A1 | 1/2002 | Pertrushin | |
| 2002/0059161 A1 * | 5/2002 | Li | G06F 16/951 |
| 2002/0143241 A1 | 10/2002 | Thorell | |
| 2004/0001616 A1 | 1/2004 | Gutta et al. | |
| 2006/0224430 A1 | 10/2006 | Butt | |
| 2009/0210228 A1 * | 8/2009 | George | H04M 3/4936 704/251 |
| 2009/0225971 A1 | 9/2009 | Miller et al. | |
| 2009/0271438 A1 | 10/2009 | Agapi et al. | |
| 2009/0299840 A1 | 12/2009 | Smith | |
| 2009/0327896 A1 * | 12/2009 | Pall | H04L 65/605 715/730 |
| 2010/0106500 A1 * | 4/2010 | McKee | G10L 13/00 704/235 |
| 2011/0038472 A1 | 2/2011 | Gartner et al. | |
| 2011/0060591 A1 | 3/2011 | Chanvez et al. | |
| 2011/0072362 A1 | 3/2011 | Denner et al. | |
| 2011/0138303 A1 * | 6/2011 | Ark | G06Q 10/10 715/753 |
| 2011/0201899 A1 | 8/2011 | Price et al. | |
| 2011/0201959 A1 | 8/2011 | Price et al. | |
| 2011/0201960 A1 | 8/2011 | Price et al. | |
| 2011/0225013 A1 | 9/2011 | Chavez et al. | |
| 2012/0054281 A1 | 3/2012 | Westmoreland | |
| 2012/0123779 A1 * | 5/2012 | Pratt | G10L 15/26 704/235 |
| 2012/0172661 A1 | 7/2012 | Chiu | |
| 2012/0323575 A1 | 12/2012 | Gibbon et al. | |
| 2012/0323579 A1 * | 12/2012 | Gibbon | G10L 15/1822 704/270 |
| 2013/0117060 A1 * | 5/2013 | Henriksen | G06Q 10/06 705/7.21 |
| 2014/0025706 A1 * | 1/2014 | Barve | G06F 40/40 707/771 |
| 2014/0082100 A1 | 3/2014 | Sammon et al. | |
| 2014/0108085 A1 * | 4/2014 | Henriksen | G06Q 10/109 705/7.19 |
| 2014/0129504 A1 * | 5/2014 | Soon-Shiong | G06F 16/951 706/47 |
| 2014/0136631 A1 * | 5/2014 | Li | H04L 51/32 709/206 |
| 2014/0316192 A1 | 10/2014 | de Zambotti et al. | |
| 2014/0365209 A1 * | 12/2014 | Evermann | G06F 40/35 704/9 |
| 2014/0380285 A1 * | 12/2014 | Gabel | G06N 20/00 717/139 |
| 2015/0110277 A1 | 4/2015 | Pidgeon et al. | |
| 2015/0142082 A1 | 5/2015 | Simon et al. | |
| 2015/0162000 A1 * | 6/2015 | Di Censo | G10L 15/22 704/270.1 |
| 2016/0077547 A1 | 3/2016 | Aimone et al. | |
| 2016/0117624 A1 | 4/2016 | Flores et al. | |
| 2016/0171062 A1 | 6/2016 | Bufe et al. | |
| 2016/0217124 A1 * | 7/2016 | Sarikaya | G06F 40/274 |
| 2018/0211659 A1 * | 7/2018 | Segal | G10L 15/22 |

* cited by examiner

SYSTEMS, APPARATUS AND METHODS FOR USING BIOFEEDBACK TO FACILITATE A DISCUSSION

This application is a continuation-in-part of U.S. Ser. No. 15/530,169, filed Dec. 8, 2016, and is incorporated herein by reference in its entirety.

FIELD OF THE INVENTION

The field of the invention is biofeedback.

BACKGROUND

The following description includes information that can be useful in understanding the present invention. It is not an admission that any of the information provided herein is prior art or relevant to the presently claimed invention, or that any publication specifically or implicitly referenced is prior art.

Biofeedback is often described as using substantially near real-time feedback signals to modify autonomic physiological functions. For example, brain waves, heart rate, breathing rate, hand temperature etc. Some researchers have pushed the envelope further, to use substantially near real-time feedback signals to modify kinetic activities that are partially under voluntary control, for example, stuttering or other speech pathologies (Electronic anti-stuttering device providing auditory feedback and disfluency-detecting biofeedback U.S. Pat. No. 6,231,500 B1), intention tremors (Clinical Application of Biofeedback Treatment with a Microvibration Transducer, *Journal of Experimental & Clinical Medicine* Vol. 12 No. 5,6, pp, S19-324, 1987), cardiac arrhythmias (The Effects of Respiratory Sinus Arrhythmia Biofeedback on Heart Rate Variability and Posttraumatic Stress Disorder Symptoms: A Pilot Study, Zucker, T. L., Samuelson, K. W., Muench, F. et al. Appl Psychophysiol Biofeedback (2009) 34: 135. doi: 10.1007/s10484-009-9085-2), incontinence (Effect of Adding Biofeedback to Pelvic Floor Muscle Training to Treat Urodynamic Stress Incontinence, Mørkved, Siv MSc, PT; Bø, Kari PhD, PT; Fjørtoft, Toril PT, Obstetrics & Gynecology: October 2002—Volume 100—Issue 4—p 730-739), temporomandibular disorders (Efficacy of Biofeedback-Based Treatments for Temporomandibular Disorders, Crider, A., Glaros, A. G. & Gevirtz, R. N. Appl Psychophysiol Biofeedback (2005) 30: 333. doi: 10.1007/s10484-005-8420-5) to name a few.

Still other researchers have used biofeedback techniques to deal with some cognitive patterns. Among other things, biofeedback techniques have been used to treat fear or anxiety ("Neurofeedback in the Treatment of Developmental Trauma: Calming the Fear-Driven Brain" by Sebern F. Fisher. W. W. Norton & Company, New York, N.Y., 2014, 416 pages, ISBN: 978-0-393-70786-1), attention deficit (Attention Enhancement System using Virtual Reality and EEG Biofeedback, B. H. Cho; J. M. Lee; J. H. Ku; D. P. Jang; J. S. Kim; I. Y. Kim; J. H. Lee; S. I. Kim, Virtual Reality, 2002. Proceedings. IEEE), alcohol abuse (Sobriety Outcome After Alcoholism Treatment with Biofeedback Participation: A Pilot Inpatient Study, International Journal of the Addictions, M. R. Denney, Jarod L. Baugh & Henry D. Hardt, Volume 26, 1991—Issue 3, Pages 335-341), smoking (Sampling of empirically supported psychological treatments from health psychology: Smoking, chronic pain, cancer, and bulimia nervosa, Compas, Bruce E.; Haaga, David A. F.; Keefe, Francis J.; Leitenberg, Harold; Williams, David A., Journal of Consulting and Clinical Psychology, Vol 66(1), February 1998, 89-112), insomnia (Biofeedback and Progressive Relaxation Treatment of Sleep-Onset Insomnia: A Controlled, All-Night Investigation, Robert Freedman and James D. Papsdorf, Biofeedback and Self-Regulation, VoL 1, No. 3, 1976), pain (Pain management in rheumatoid arthritis patients, Parker, J. C., Frank, R. G., Beck, N. C., Smarr, K. L., Buescher, K. L., Phillips, L. R., Smith, E. I., Anderson, S. K., Walker, S. E., Arthritis & Rheumatology, Volume 31, Issue 5, May 1988, Pages 593-601), and socially undesirable behaviors, as in for example, aggressive thoughts of sexual predators (Sexual recidivism among child molesters released from a maximum security psychiatric institution, Rice, Mamie E.; Quinsey, Vernon L.; Harris, Grant T., Journal of Consulting and Clinical Psychology, Vol 59(3), June 1991, 381-386).

All publications referenced herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Despite all of this focus on disease amelioration and psychophysical therapies, it appears that biofeedback has never been applied to assist with more every day, common experiences, including for example guiding business meetings (Dynamic media augmentation for presentations, US 20090327896 A1), assisting with invention brainstorming sessions ((Effects of Simulated Biofeedback and Human Monitoring on Brainstorming Performance, Graham, William K., The Journal of Social Psychology, Volume 101, 1977—Issue 1, Pages 139-143), mediating disputes, helping people get to know each other, accelerate their learning (Electroencephalograph based biofeedback system for improving learning skills, U.S. Pat. No. 6,626,676 B2), and providing guidance with respect to other goal oriented discussions.

Biofeedback has also apparently not taken advantage of artificial intelligence (AI) systems, which can conceivably be used to guide the feedback signals.

AI has been employed to assist humans in cognitive functioning, but not using biofeedback. For example, the CALO (Cognitive Assistant that Learns and Organizes http://www.ai.sri.com/project/CALO) project funded by the Defense Advanced Research Projects Agency (DARPA) has facilities for organizing and prioritizing information, preparing information artifacts, mediating human communications, task management, scheduling and reasoning, and allocating resources. Spin-offs from this project include Siri™ (now an Apple™ product), Social Kinetics, a social application that learned personalized intervention and treatment strategies for chronic disease patients; the Trapit project, which is a web scraper and news aggregator that makes intelligent selections of web content based on user preferences; Tempo AI, a smart calendar; Desti, a personalized travel guide; and Kuato Studios, a game development startup. Yet because CALO applications don't utilize biofeedback, they cannot provide substantially near real-time feedback to human users who are seeking cognitive assistance; especially during an interactive discussion.

Thus, although some technologies utilize biofeedback, other technologies assist humans in cognitive functioning, and still other technologies use AI, it appears that no one has so far figured out how to utilize biofeedback to assist humans in their cognitive functioning during discussions with other humans or machines.

SUMMARY OF THE INVENTION

The inventive subject matter provides systems, apparatus, and methods in which biofeedback is used to facilitate discussions. Preferred embodiments include the steps of sequentially (a) identifying a concept used by at least one of the participants during a discussion, (b) sourcing additional content from outside the discussion, (c) detecting use of a trigger expression by one of the participants, and then (d) further to detecting use of the trigger expression, rendering at least some of the additional content to one or more of the participants as an electronic biofeedback signal. In especially preferred embodiments, steps (a) through (d) are executed in a repeating loop.

Trigger expressions can be single words or multiple word phrases, which might or might not have particular relevance to any concepts being discussed by the participants. For example, contemplated trigger expressions include "now", "computer, give me some help here", "any further ideas", and "I'm stuck". In narrow embodiments, trigger expressions can be limited to exclude question and instruction words and phrases that one might use in operating such devices as Amazon's Alexa®, Apple's HomePod®, and apps such as Siri® and Cortana®.

Trigger expressions can also be non-verbal expression characteristics, including for example snapping of fingers, or smiling.

In many embodiments discussions will involve multiple concepts, and therefore multiple externally sourced contents, and multiple electronic biofeedback signals. In such instances the same trigger expression(s) could be used to trigger different electronic biofeedback signals, and in some instances different trigger expressions could be used to trigger different electronic biofeedback signals.

Sourcing of additional content can be facilitated in many different ways, including by utilizing one or more of: (a) profile information of any of the participants; (b) expression characteristics of any of the participants; and (c) responses to questions posed by an electronic processing system. Sourcing of additional content can advantageously be accomplished by an artificial intelligence (AI) system. In other aspects, sourcing of additional content can be facilitated by symantically expanding terms used by any of the participants in expressing the concepts, and/or using terms expressed by any of the participants to make a 2nd order correlations.

Contemplated $2^{nd}$ Order Correlations are exemplified in pending U.S. application Ser. No. 14/091,874 (Fish).

Electronic biofeedback signals can be rendered to any of the participants in any suitable manner, including for example, a visual image rendered by a virtual reality headset or other device, an electronically generated auditory sound, rendered through earphones or speakers, other tactilely perceptible vibration or other movement. Electronic biofeedback signals might or might not have sufficient intensity to elicit a perceptible pain response from the participant.

Electronic biofeedback signals can be rendered to one or more of the participants as computer-generated graphical images, which are preferably created de novo during the discussion. To avoid interrupting train of thought of the participants, electronic biofeedback signals can advantageously be delayed pending a lull in the discussion, or according to some other parameter.

Contemplated electronic biofeedback signals can also include summaries and agendas.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
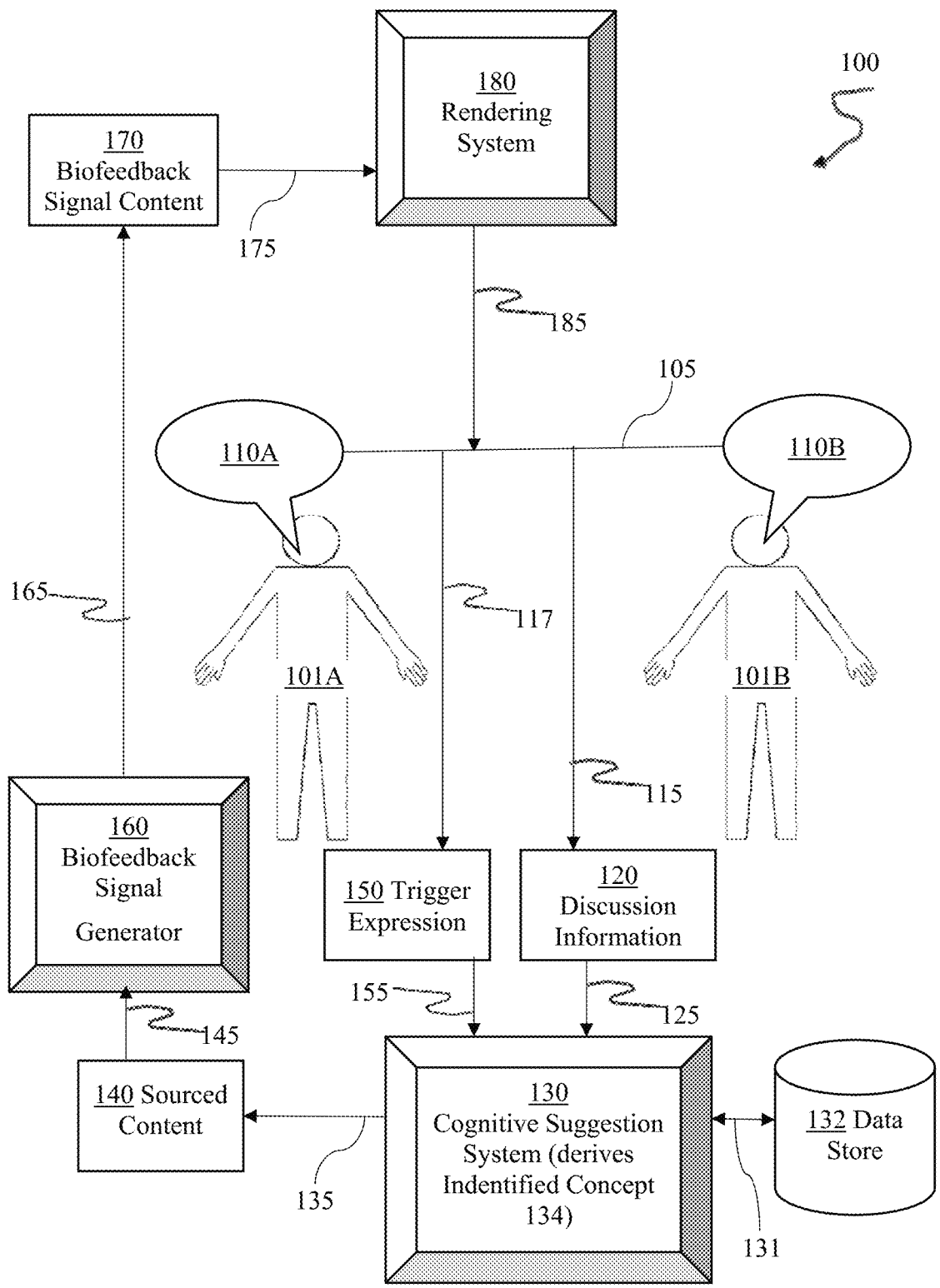
FIG. 1 is a diagram of at least two participants engaged in a discussion with each other, in which a computing system provides biofeedback during the discussion to at least one of the participants.

In some embodiments, the numbers expressing quantities of ingredients, properties for example concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patent ability. When any such inclusion or deletion occurs, the specification is herein deemed to contain the group as modified thus fulfilling the written description of all Markush groups used in the appended claims.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used herein, the term "biofeedback" means using electronics to monitor a physiological function of a person, and using the acquired information to provide a signal to the person, in substantially near real-time, with a goal of assisting the person to alter the function. Contemplated physiologic functions include brainwaves, muscle tone, skin conductance, heart rate, breathing, hand, body and face expressions, and speech. The alteration of function could be conscious or unconscious.

As used herein, the term "discussion" means an exchange of information between at least first and second participants in which there is no lull for a consecutive one hour period.

As used herein, the term "lull" means a temporary interval of relative quiet or relative lack of activity. Under this definition, a lull in a discussion would be an interval in which none of the participants is speaking verbally or entering text to another participant in the discussion.

As used herein, the term "speech" means verbal expressions using a communication, whether rendered auditorily, through typing, sign language, or any other manner, plus hand gestures or other expression characteristics, which are considered herein to have no commonly accepted, specific language equivalent. As used herein, the term "expression characteristics" include, for example, facial expressions, hand motions, eye movements, and body movements, to the extent that they have communicative meaning.

As used herein, the term "concept" means a mental representation of one or more facts or ideas, plans, or intentions.

As used herein, the term "content" means information that a computing system can express in a human perceptible format, including for example auditory, textual or graphic formats. This includes, for example, beeping, music, spoken words and other sound signals, as well as flashing lights, images, video and other visually perceptible light signals.

As used herein, the term "trigger expression" means a pattern of expression used to trigger an action. In preferred embodiments, trigger expressions are spoken words or phrases, finger or hand movements.

As used herein, the term "derived content" is subject matter pertaining to the concept (mental representation) detected from the first participant. Derived content can be a concept definition, references where a concept is explained or examined, or other material related to the concept in the discussion. It can also be an expansion of a concept that is likely to include other concepts as part of the derived content.

As used herein, the term "artificial intelligence system" means a system that simulates human intelligence by learning and/or making inferences.

As used herein, the term "biosignal" means any signal in a living being that can be measured and monitored. Biosignals can be bioelectrical signals, but they can also be electrical and non-electrical signals.

As used herein, the term "listen" is to pay attention to someone or something in order to hear what is being said, sung, played, typed, or emitted.

As used herein, the term "includes" means "includes, but not limited to".

The technical problem being addressed herein is how to use electronics to help participants communicate during discussions. The technical solution is to use biofeedback signals to provide additional information to one or more of the participants during the discussion. In some embodiments at least some of the biofeedback signals are derived in part using output from an AI System.

FIG. 1 generally includes at least first and second participants 101A, 101B, engaged in a discussion 101A, 101B, with each other. A Cognitive Suggestion System (CSS) 130 receives Discussion Information 120, and extracts, infers or otherwise derives a concept from that information, and then sources related content 140 at least partially from a data store 132. Upon receipt of a Trigger Expression 150 from at least one of the participants 101A, 101B, the Cognitive Suggestion System 130 sends content 140 to Signal Generator 160, which then produces Biofeedback Signal Content 170. Rendering System 180 renders the Biofeedback Signal Content 170 to at least one of the participants 101A, 101B.

Various communication lines carry Discussion Information 120, a Trigger Expression 150, Sourced Content 140, and Biofeedback Signal Content 170. All suitable communication lines are contemplated, including for example, Internet, WiFi, Bluetooth, near-field, or telecommunications bands or any combination of line/radio, simplex/duplex, analog/digital, or baseband/carrier communication systems. The preference being the Internet coupled with telecommunications bands enabled by standardized protocols to send portions of speech and biosignals over any distance.

Both participants 101A and 101B are nominally depicted as humans in FIG. 1, but should be interpreted euphemistically as including humans and/or non-humans, e.g., system software agents. It is also contemplated that additional participants (not shown) could take part in the discussion, and FIG. 1 should be interpreted to optionally include at least one additional participant. In preferred embodiments, at least one of participants 101A and 101B is a human.

It is contemplated that discussions can take place face to face, as in a physical meeting between participants 101A, 101B, remotely using any sort of telecommunications, or any combination thereof. Contemplated discussions can also occur with lulls, of several second, several minutes, or even several hours. In preferred embodiments, discussions have no lulls greater than one hour.

Since there can be more than two participants in a discussion, the term "between" is used herein to mean both "between" and "among".

In embodiments of the current subject matter, the CSS 130 actively "listens" to and/or "watches" the participants 101A, 101B in the discussion. This should not be seen as an extraordinary usage of those terms, because in current parlance devices such as Amazon's™ AleXa™ "listens" to words spoken in a room, and certainly some televisions and other computing systems are used to "watch" activities taking place in their fields of view.

The discussion contributed by participants 101A, 101B is represented by their discussion output as 110A and 110B respectively. The discussion components, as already stated, can be comprised of what is said, sung, played, typed, or emitted including expression characteristics. See also paragraph 81 in the priority application, Ser. No. 15/530,169 for more on expression characteristics.

The Discussion Information 120 can be derived from any suitable segment or length of the discussion. For example, the CSS 130 might derive a concept from only a few key words that it recognizes as denoting a concept. Thus, a participant 101A or 101B might say "The key concept or Concept Nexus here is agriculture", and the CSS 130 could thereby infer that the Identified Concept 134 is "agriculture". Alternatively, the CSS 130 might listen to a fifteen minute discourse on propagation of strawberries, and thereby infer that the Identified Concept 134 is "agriculture" and/or "strawberries" and/or "propagation". CSS 130 could identify multiple overlapping concepts 134, as in the previous example.

Identified Concepts 134 are counted by the CSS 130 and that count is retained for each Identified Concept 134 during the discussion or, when in use, the discussion time frame window. Identified Concept 134 counts are then used by the CSS 130 when considering Relevance Frequency, Relevance Intensity, Concept Nexus in a Concept Map, and possibly other uses depending on the embodiment and domain.

Cognitive Suggestion System (CSS) 130 can comprise any suitably programmed or trained computing system, which could advantageously include an AI component. CSS 130 communicates with Data Store 132, which also advantageously includes an AI component. Data Store 132 could be anything from a defined, proprietary data source to the entire Internet accessible web or other publically accessible source of information.

The CSS 130 receives text, video and/or audio comprising the discussion identifying concepts 134. The CSS also detects a Trigger Expression. The CSS uses the Identified Concept(s) 134 and they are affected by the Trigger Expression 150 to source Sourced Content 140 related to the Identified Concept 134.

The operation of Cognitive Suggestion System (CSS) 130 in some preferred embodiments may also be configured in one or more ways. Some configuration settings can be actuated during system design whereas other configuration settings in some embodiments may allow participants 101A, 101B to configure a setting for one or more parameters. A discussion time frame window can be set so that the CSS will consider only Identified Concepts 134 and Trigger Expressions 150 that occur during this time frame window. Trigger Expression 150 can be stipulated either specifically or by category or by any other suitable means of selection. When considering the operation of Trigger Expressions, a Relevance Frequency Threshold and or a Relevance Intensity Threshold can be configured. CSS settings may also be configured to impact the way concepts are used by the system. Concept Weighting can be set to change over time during a discussion, Concept Relevance mapping methodologies can be selected, and the parameters for a Concept Nexus can be delineated. Additionally, some preferred embodiments may provide the means for participants 101A, 101B to configure their biofeedback preferences as graphical images, data representations, voice responses or other sounds or beeps, lighting changes or flashes or any other digitally generated output. In cases where participants 101A, 101B can set some configuration parameters, some of these parameters might be changed during an active discussion. i.e., as in the type of or exact phrases of the Trigger Expressions 150.

The Data Store 132 is a data storage device that can be a database or other content management system configured to support Cognitive Suggestion System (CSS) 130 operations. The Data Store 132 can be domain dependent containing structured knowledge for the specific domain or be a more general purpose data store that would contain structured knowledge for a wide-range of everyday or commercial applications. The knowledge structure of the Data Store 132 is integral to its operations and understanding of Concept Relevance. Some preferred embodiments may require ontologies, taxonomies, semantics, controlled vocabularies, knowledge graphs, statistical models, and domain specific content to be used by the CSS 130 and in the case of CSS 130 being an AI system, the some of the structured knowledge will be learned by the CSS 130. CSS 130 system defined and participant define configurations will be managed in the Data Store 132.

When considering the sequence of identifying a concept 134 and at some subsequent point detecting a Trigger Expression 150, some preferred embodiments may use elapsed time during a discussion as a Cognitive Suggestion System 130 parameter. The elapsed time during a discussion could be considered as sequential time slices or taken as a period of sequential time during a discussion as a time frame window; the frame having clear time boundaries such as start, stop, and elapsed time. The Identified Concepts 134 that have been identified during the active time frame window are those concepts that are assessed for relevance and can also be used to source Sourced Content 140 when an appropriate Trigger Expression 150 has occurred. In embodiments where a time frame window is used, Identified Concepts 134 that occurred earlier than the active time frame window may not be considered to source Sourced Content 140. As suggested here, the length of time that constitutes a time window or time frame window can be system configurable or even in some embodiments be configurable by the participant 101A or 101B for a particular discussion.

As an example of how the time frame window would function, let's consider participants 101A, 101B using a Cognitive Suggestion System (CSS) 130 that is configured so that a time frame window is 15 minutes. The start of the discussion, when one of the participants 101A or 101B begins speaking, initiates the time frame window clock. The time frame window clock continues to track time elapsed during the conversation for a total of 15 minutes. At this point, all of the subject matter of the discussion so far is pertinent for use by the CSS. At minute 16 of the discussion, the time window would remove Identified Concepts 134 that had been identified within minute 1 (one) of the discussion and would now include Identified Concepts 134 that were part of the discussion during minutes 15-16 along with minutes 2-15 of the discussion.

In looking at how far back in time the Cognitive Suggestion System (CSS) 130 goes to identify a concept 134 and subsequently detect a Trigger Expression 150, we return to the example where a participant 101A or 101B spoke about strawberries between 10 and 15 minutes ago (segment 1 and Identified Concept 134 #1). During the last 10 minutes (segment 2 and Identified Concept 134 #2), the participant 101A or 101B discussed cars. The participant 101A or 101B then says a Trigger Expression 150, or "banana" or "on topic?" detected by the CSS 130.

In other words, the time frame or time frame window shifts at one minute increments as a time decay process to remove or not include the oldest 1 minute of Identified Concepts from CSS 130 for this discussion and add the newest minute of Identified Concepts 134 to the CSS 130. (rolling time frame window). Therefore, in some preferred embodiments that use a time frame window during a discussion defines an Identified Concept 134 relevance time frame window that affects what the Trigger Expression 150 is applied to when sourcing Sourced Content 140.

When we consider the time decay of a 15 minute time frame window that can be configured to operate during a discussion, we can return to the strawberry supply chain example. The participants 101A, 101B discuss strawberry-related things comprising 100 usages of "strawberry" as a key concept or Concept Nexus for perhaps 345 seconds. During the subsequent 555 seconds of the 15 minute time frame window of the discussion, these concepts are identified 134 as follows: melons 2 times, cars and other vehicles 12 times, boats 11 times, and drones 4 times. As the Identified Concepts 134 strawberries and melon would be weighted as less relevant due to the time decay effect on Concept Weighting, the key concept in this case might shift to a concept of vehicles used in the supply chain.

Trigger Expression 150 can be selected using the Suggest-Assert-Modify methodology discussed in "Suggest-Assert-Modify: A Taxonomy of Adaptive Scaffolds in Computer-Based Learning Environments" by James R. Segedy, Kirk M. Loretz, and Gautam Biswas. Suggestions may include trigger expressions aligned with categories such as goal orientation, explanation construction, prediction, planning, or reflection. Assertions may include trigger expressions aligned with categories such as problem domain, cognitive process, metacognitive strategy, or learner behavior.

Contemplated Trigger suggestions include:
a. Goal-oriented—on-topic, system asks what is your goal?
b. Explanation—concepts are pieces of a whole either logic or tangible item
c. Prediction—source evidence of outcomes
d. Planning—source step-by-step
e. Reflection—source the most used connection which 2 concept nodes have been used most and are connected (or not)

Contemplated Assertions include:
a. Problem domain—comment on current concept nexus—State that this is the core (and wait for discussion confirmation)
b. Cognitive process—snapshot of used concepts and related concepts. You were talking about this, but you should cover this as well.
c. Metacognitive strategy—Are concepts expanding or focusing? "I see you are covering many things. Maybe you want to focus on just . . . "
d. Learner behavior—guidance—"You know about this and this, but don't have a good understanding of . . . this"

Trigger Expressions 150 can be dependent on the particular embodiment in a particular domain; for example when using the CSS 130 to aid a participant 101A or 101B in designing a chair a trigger expression might be "fit" as in "does it fit". Trigger Expressions 150 may also consist of CSS 130 either system or user pre-defined "random" words or phrases such as "banana" or "on topic?". Trigger Expressions 150 may also be set to operate at particular times during a discussion as an example, every 10 minutes.

Trigger Expressions 150 may also be set to respond to the Relevance Frequency of a concept, where a Threshold of how many times in the discussion time frame window a concept has been identified is not necessarily keyword based. To continue with the agriculture/strawberry example above, the relevance frequency is set at 25. The CSS 130 has identified the strawberry concept 24 times over the 10 minute duration of the discussion so far. During the next minute duration of the discussion, strawberry is said again—for the $25^{th}$ time during the discussion time frame window. Hence, a trigger expression has now been detected, and the CSS 130 could combine this trigger expression information with the Identified Concept 134 to source Sourced Content 140.

It is also contemplated that a Trigger Expression 150 could be used to affect Relevance Intensity. Relevance Intensity is a measurement of how often an Identified Concept 134 has been used in a discussion relative to other Identified Concepts 134 as in a percentage of one Identified Concept with respect to other Identified Concepts within a very small window of time, e.g. 1 minute. In this use of a Trigger Expression 150, when a Threshold comparative percentage of an Identified Concept 134 has exceeded X % at a particular relevance intensity window of time, a trigger expression can be detected.

An example of a Relevance Intensity Threshold Trigger Expression 150 occurring could happen when talking about the strawberry supply chain. The intensity relevance threshold in the Cognitive Suggestion System 130 is set at a threshold of 50%. Participants 101A, 101B in a discussion have been talking about growing strawberries and preparing them to go to market. During the particular relevance intensity time window the concepts in the discussion are distributed as follows: strawberries 30%, crates 10%, sorting 5%, trucks 55%. A trigger expression is detected because the trucks Identified Concept 134 comprise over 50%.

Concept Relevance is determined by the Cognitive Suggestion Tool (CSS) 130 using one or more methods in preferred embodiments. One aspect of Concept Relevance can be based on the position of the Identified Concept 134 as a node connected to other nodes in an ontology. Another aspect that can be considered important in particular embodiments could be the result of queries made to knowledge systems that typically respond with related concepts, where each of these concepts are assigned a probability of relationship to the Identified Concept 134. Concept weight is a term commonly used when considering output from knowledge systems queries so here we use the terminology Concept Weighing to differentiate the CSS 130 Concept Weighting from an AI system returned concept weight.

Returning to the strawberry supply chain example, Concept Relevance can be used by the CSS 130 in order to derive the key concept or Concept Nexus during a particular time frame window during the discussion. The participants 101A, 101B discuss strawberries 5 times, melons 2 times, cars and other vehicles 10 times, boats 15 times, and drones 7 times. It would seems that the discussion has moved away from strawberries, but based on the Concept Relevance at the particular time in the discussion the CSS 130 can determine that the key concept might still be strawberries and that the concepts of cars, vehicles, boats, and drones are relevant because of the delivery aspect of the strawberry supply chain. The concept melons, somewhat closely relevant to strawberries does not become the key concept as it occurs in the discussion less often than strawberries.

In some preferred embodiments, a Relevance Threshold setting can signify whether the embodiment is set to source Sourced Content 140 more broadly or more narrowly. The Relevance Threshold setting can be affected by either the node distance or concept probability as just discussed.

When considering the ontological node distance connecting concepts, a Relevance Threshold could be considered. An example of a broad Relevance Threshold setting is where nodes that are within 5 nodes of the Identified Concept 134 node are in the ontology, and included in the Concept Map. An example of a narrow Relevance Threshold is where nodes are considered relevant only if they are within 2 nodes of the Identified Concept 134 in the ontology representation.

One way that the CSS 130 could broaden or narrow concept node inclusion, and thereby set a Relevance Threshold, is by adjusting a likelihood/assurance percent value. The value could be set to a lower percentage to capture a wider range of concepts, and set to a higher percentage value to narrow the range of concepts included in the concept map.

Returning to the discussion of a time frame window during which concepts are considered by the Cognitive Suggestion Tool 130, Concept Weighting can also be associated with a time aspect. During the previously suggested time frame window of 15 minutes, a concept can be assigned a weighting related to concept relevance and that weighting can also be affected in a manner of time decay. A Concept Weighting at the time of the Identified Concept 134 at minute 1 of the 15 minute time frame window would be associated with the full concept weighting. As this Identified Concept "ages" (the Identified Concept 134 was said at time 1 and we are now at time 10 in the time frame window), the concept weighting will be reduced by some number, getting less and less weighting during the time frame window unless the Identified Concept 134 is spoken again that would refresh that Identified Concept 134 to be associated with the full concept weighting. As an example, the Identified Concept 134 is "strawberries" that has a concept weighting of 15 when it is first identified in the time frame window. As each minute of the discussion transpires, the concept weighting decreased by 1 so that at minute 10 of this time frame window "strawberries" is now associated with a concept weighting of 5.

Although a finite time frame window setting can be useful in some preferred embodiments, a time frame window may also be set in some embodiments to infinite whereby other configurations would need to be set in such a way in order to achieve the sourcing desired Sourced Content 140.

When considering Concept Relevance, a Concept Map can be used by the Cognitive Suggestion Tool 130 to hold a graphical representation of the Identified Concepts 134 and their relevant concepts. The graphical representation format may vary depending on the embodiment, but the representation would contain elements for each of the concepts active during the time frame window and each of these concept would have values associated with it to represent which other concept or concepts it was directly connected to in the graph. This graph can be a view of Concept Relevance.

In preferred embodiments using a Concept Map, a Concept Nexus can be defined. A Concept Nexus is the concept, either an Identified Concept 134 or a CSS 130 derived concept that is considered to be the focal point of the discussion within the current time frame window of that discussion.

Sourced Content 140 is preferably quite limited so that it could relatively easily be configured by the Biofeedback Signal Generator 160 into the Biofeedback Signal Content 170. To continue with the agriculture/strawberry example above, the Sourced Content 140 could be an image of strawberry runners, fertilizers, or weather reports or other guidance on when it might be best to propagate strawberries.

The Sourced Content 140 could also be affected in some manner by the Trigger Expression 150. For example, one of the participants 101A or 101B might talk about "watering frequency", and that might cause the CSS 130 to select the Sourced Content 140 to be weather-related instead of fertilizer-related. The CSS 130 could make that decision based upon the AI component.

In some preferred embodiments, the Cognitive Suggestion System (CSS) 130 can be configured to source Sourced Content 140 directly reflecting Identified Concepts 134 from the participants' 101A, 101B discussion. An example where this can be helpful to participants 101A, 101B is during discussions where the participants want to be kept aware of concepts or topics covered during the discussion. In this example, the CSS 130 could be configured to tell the participants 101A, 101B at the end of each 10 minute (configured) time frame window what topics they have discussed during the past 10 minutes. Here the Trigger Expression 150 is set by default to 10 minutes and the CSS 130 sources Sourced Content 140 comprising the aggregate of 10 minutes discussion of Identified Concepts 134. In the same example, the Trigger Expression 150 might be participant defined as "Topics?" where the CSS 130 will similarly source the Identified Concepts 134 during the current time frame window as Sourced Content 140.

Other preferred embodiments can be configured to set the Relevance Threshold more broadly whereby the Cognitive Suggestion System 130 sources concepts with a lower Relevance Threshold (lower percentage weighting) so that more concepts are available by the CSS 130 for consideration for Sourced Content 140. In embodiments where this setting is active, the CSS 130 can source Sourced Content 140 that has not directly been contained in the current discussion time frame window, but can be of interest to the participants 101A, 101B. Here the Sourced Content 140 can be in the form of concept suggestions that will be rendered as biofeedback to participants 101A, 101B.

As an example of this embodiment, the participants may have been discussing restaurant etiquette. The Identified Concepts 134 pertain to the social aspects of fine dining such as the arrangement of silverware, use a napkin, and how to hail a waiter or sommelier. As the Cognitive Suggestion System 130 has been configured to make suggestions every 5 minutes into the discussion, at the 5 minute mark, the CSS 130 sources Sourced Content 160 that is a suggestion about fine dining behavior. The Sourced Content 140 is resolved by the Biofeedback Signal Generator 160 into Biofeedback Signal Content 170. Then, the Rendering System 180 makes a suggestion, speaking into earpieces worn by each of the participants 101A, 101B saying, "Make sure you use your butter knife to butter your bread."

Biofeedback Signal Generator 160 produces Biofeedback Signal Content 170. Signal Generator 160 can be an electronic device or a computer system configured to accept a Sourced Content 140, determine the appropriate Biofeedback Signal Content 170, and then generate the appropriate signal. The Biofeedback Signal Content 170 can consist of any form of digital signal that humans can perceive yet is usually visual, audible, or tactile in nature. In some preferred embodiments, the Biofeedback Signal Content may consist of more than one signal conveying the same content or information as in an image of strawberries and an audio file describing what strawberries are and how they grow.

An example of signals generated by the Biofeedback Signal Generator 160 can be when beeps and flashes are generated when the Identified Concept 134 is a weather-related concept and the Trigger Expression 150 is "on topic?" The beeps or flashes generated by the Biofeedback Signal Generator 160 are more than prior art US 2009/0271438 (Agapi—Signaling Correspondence Between a Meeting Agenda and a Meeting Discussion) which just looks for key words against agenda. The difference here because their system beeps whenever keyword is spoken, but ours is silent until the Trigger Expression 150 is spoken or is generated automatically by the Cognitive Suggestion System 130 based on a configuration setting.

Another example of signal generation by the Biofeedback Signal Generator 160 continues the example when the participants 101A, 101B have been discussing planting strawberries. The Cognitive Suggestion System (CSS) 130 knows of the participants' 101A, 101B location. In this example, perception words i.e., like wonder and think are some of the Trigger Expressions 150. When one of the participants says, "I wonder when I should plant strawberries this year? I think it is in May." The CSS detects the trigger expression and sources the appropriate Sourced Content using the participant's 101A or 101B location as an Identified Concept 134. As the participants 101A, 101B have set the CSS 130 configuration to receive suggestions when trigger expressions are said, the Biofeedback Signal Generator 160 knows that a voice signal is requested and generates the Sourced Content 140 into the appropriately generated biofeedback signal as Biofeedback Signal Content 170. The Rendering System 180 then renders as an audio signal the suggestion, "The best time to plant strawberries is early spring for Southern California. You are already too late" See also paragraph 133 in the priority application, Ser. No. 15/530,169 for more on perception words.

Rendering System 180 receives the Biofeedback Signal Content 170 that was generated by the Biofeedback Signal Generator 160. The Biofeedback Signal Content is delivered in a format that can be recognized by the Rendering System 180, and subsequently rendered to the participants 101A and 101B using the digital devices and equipment that are available and accessible to them during the discussion. Participants 101A, 101B can have advantageously configured their biofeedback devices and equipment prior to their discussion, or use devices or equipment provided to them that are already configured to work with the Rendering System 180. The Rendering System 180 is either pre-configured for rendering specific types of Biofeedback Signal Content 170 or is can be able to detect participant devices or equipment.

An example of another Biofeedback Signal Content 170 format that can be rendered by the Rendering System 180 returns to the example of growing strawberries. The current participant 101A, 101B discussion is about how to propagate strawberries, and when during the growing season this should occur. The Cognitive Suggestion System (CSS) 130 in this example is configured to monitor Relevant Concepts in the 10 minute time frame window. The CSS 130 currently has the key concept or Concept Nexus of strawberry propagation. At the 10 minute time frame window, the Trigger Expression, the Sourced Content 140 consists of images of the current weather patterns, an article on strawberry propagation and a video showing what strawberry rhizomes look like and where to prune them away from the parent plant. The Biofeedback Signal Generator 160 bundles the Sourced Content 140 into a Biofeedback Signal Content 170 that is understood by the Rendering System 180. Participants, who are in front of their display devices, thereby have the weather maps, strawberry article, and propagation video rendered to them on their devices as they continue their discussion.

In yet another example, the Rendering System 180 can be configured by the Cognitive Suggestion System (CSS) 130 to render a buzzing sound to participants 101A, 101B as a notification of contra-indication of subject matter discussed during the discussion. In this example, the CSS 130 has been configured to stop the participants 101A, 101B from including particular Identified Concepts 134 in their discussion. Here the Trigger Expression 150 is that the Identified Concept 134 was outside the concepts allowed for the discussion. The Sourced Content 140 is a message to sound the buzzer for the participants 101A, 101B. The Biofeedback Signal Generator 160 initiates the buzzer code that is the Biofeedback Signal Content 170 that is then rendered to the participants 101A, 101B by the Rendering System as a buzzing sound.

Another example of the Cognitive Suggestion System (CSS) 130 being useful in everyday situations is one where two participants 101A, 101B are enjoying a coffee in a coffee shop that has Wi-Fi capability. Each of the participants 101A, 101B has their own mobile phones with them and have configured the CSS 130 to know of their individual phone numbers and that they have earbuds that will enable them to hear sounds emanating from their phones. In this example, the participants 101A, 101B are discussing an upcoming conference that both participants plan on attending. The current focus or Content Nexus of the discussion is on the keynote speaker for the conference. A participant 101A or 101B is commenting that the keynote speaker got their PhD at XYZ University. As the Trigger Expression configuration in the CSS 130 is set to "problem domain", the concept nexus of discussion about the keynote speaker triggers Sourced Content 140 about the speaker. The Biofeedback Signal Generator 160 receives textual and audio information that is Biofeedback Signal Content. The Rendering System 180 renders an audio comment on the speaker's background to participant 101A: "Did you know that Speaker A went to WhatsamattaU for their undergraduate degree?" This is pertinent to the participants 101A, 101B because WhatamattaU is located in their hometown. At the same time, participant 101B receives a text message on their phone that is a URL for a website about Speaker A as well as a recent picture of the speaker. Now participant 101A and 101B can continue to enjoy their coffee and learn more about the wonderful speaker that they will soon hear opine.

Communications lines 115 and 125 carry the discussion segments 110A from participant 101A and 110B from participant 101B respectively to the Cognitive Suggestion System (CSS) 130 as an Identified Concept 134. Communication lines 117 and 155 carry the discussion segments 110A from participant 101A and 110B from participant 101B respectively to the Cognitive Suggestion System (CSS) 130 as a Trigger Signal 150.

Communication line 131 carries Cognitive Suggestion System (CSS) 130 requests to the Data Store 132 and the Data Store uses communication line 131 to transfer data to the CSS 130.

Communication lines 135 and 145 carry the Sourced Content 140 from the Cognitive Suggestion System 130 to the Biofeedback Signal Generator 160.

Communication lines 165 and 175 carry the Biofeedback Signal Content 170 from the Biofeedback Signal Generator 160 to the Rendering System 180.

Communication line 185 carries the rendered biofeedback signal content to the participants' 101A, 101B digital devices; thereby making suggestions into the participants' 101A, 101B discussion.

Figure 2:
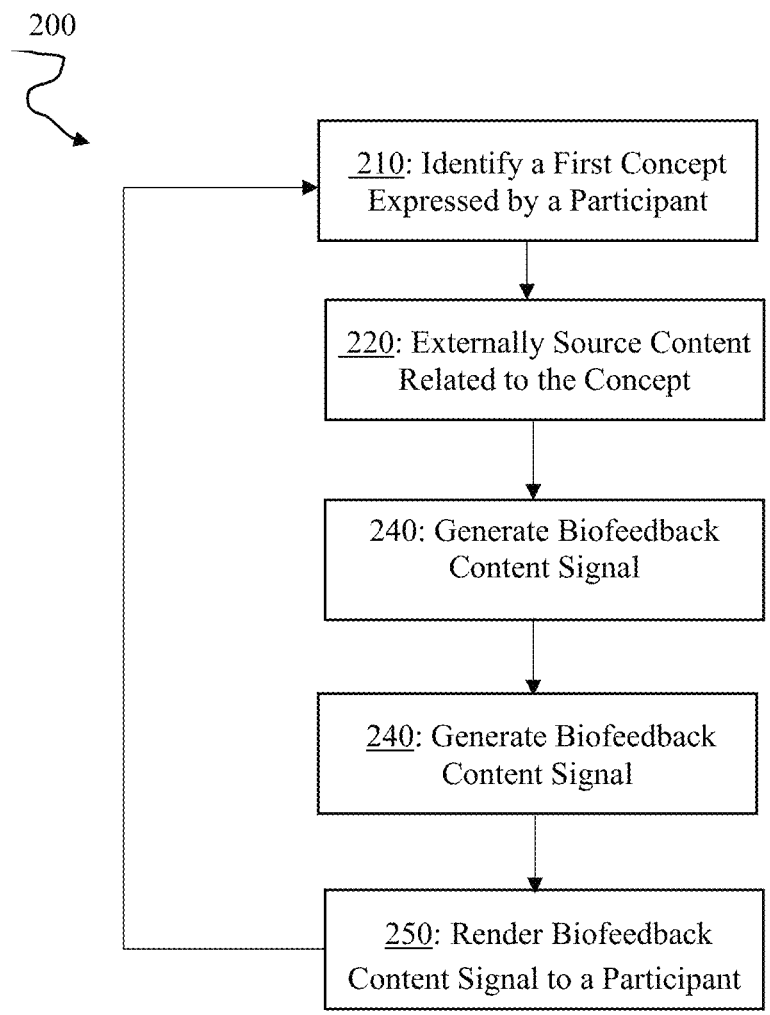
FIG. 2 is a flowchart depicting steps taken by the Cognitive Suggestion System (CSS) depicted in FIG. 1.

FIG. 2 is a flowchart 200 depicting steps taken by the Cognitive Suggestion System e.g. 130 in FIG. 1 that has identified a concept from a participant discussion, detected trigger expressions from the participant discussion, sourced content related to the identified concept and detected trigger expression, generated biofeedback signal content, and rendered that biofeedback content to one or more participants as a suggestion or assertion into the discussion as electronic biofeedback signal.

At step 210, The Cognitive Suggestion System (CSS), e.g. 130 in FIG. 1, identifies a concept from a discussion. The CSS e.g. 130 in FIG. 1 "listens" and/or "watches" the participants e.g. 101A, 101B in FIG. 1 in the discussion. The Identified Concept e.g. 134 in FIG. 1 can be derived from any suitable segment or length of the discussion.

At step 220, content related to the Identified Concept, e.g. 134 in FIG. 1, is sourced externally. The Cognitive Suggestion System (CSS), e.g. 130 in FIG. 1, accesses the Data Store; e.g. 132 in FIG. 1, to source related or relevant concepts. The Data Store, e.g. 132 in FIG. 1, maintains a structured view of concept relationships, possibly via an ontology, that is used to source relevant concepts and related information from the data store for use by the CSS, e.g. 130 in FIG. 1.

At step 230, a Trigger Expression e.g. 150 in FIG. 1 contributed by participant e.g. 101A or 101B in FIG. 1 is detected by the Cognitive Suggestion System (CSS), e.g. 130 in FIG. 1. The nature of what constitutes a trigger expression is either pre-configured in the Data Store, e.g. 132 in FIG. 1 or is set dynamically by participant, e.g. 101A or 101B in FIG. 1. Depending on the type of trigger expression used by the particular embodiment, a time frame window, also either pre-configured or set dynamically as already described here, can be used by the CSS, e.g. 130 in FIG. 1 to determine when a trigger expression has been detected.

At step 240, a Biofeedback Content Signal, e.g. 170 in FIG. 1, is generated from the Sourced Content, e.g. 140 in FIG. 1. The Sourced Content is derived by the Cognitive Suggestion System (CSS), e.g. 130 in FIG. 1, based on the Identified Concept, e.g. 134 in FIG. 1 and the Trigger Expression, e.g. 150 in FIG. 1. The Sourced Content is sent from the CSS to the Biofeedback Signal Generator, e.g. 160 to formulate the Biofeedback Content Signal, e.g. 170 in FIG. 1.

At step 250, a Biofeedback Content Signal, e.g. 170 in FIG. 1 is rendered to a participant, e.g. 101A or 101B in FIG. 1. The Biofeedback Content Signal may contain multiple digital formats that the Cognitive Suggestion System, (CSS), e.g. 130 in FIG. 1, "knows" are acceptable digital formats that the participants, e.g. 101A, 101B in FIG. 1, can receive on their devices or equipment. The CSS knowledge of these participant devices has been configured in the Data Store, e.g. 132 in FIG. 1. The Rendering System, e.g. 180 in FIG. 1, can be aware of which participant is using which device type in order to ensure that the Biofeedback Content Signal, e.g. 170 in Figure being rendered to that participant is appropriate. The Rendering System may render one or more digital artifacts to one or more participants or it may deliver one or more digital artifacts to participant, e.g. 101A in FIG. 1 and an entirely different or somewhat different set of digital artifacts to participant, e.g. 101B in FIG. 1.

Figure 3:
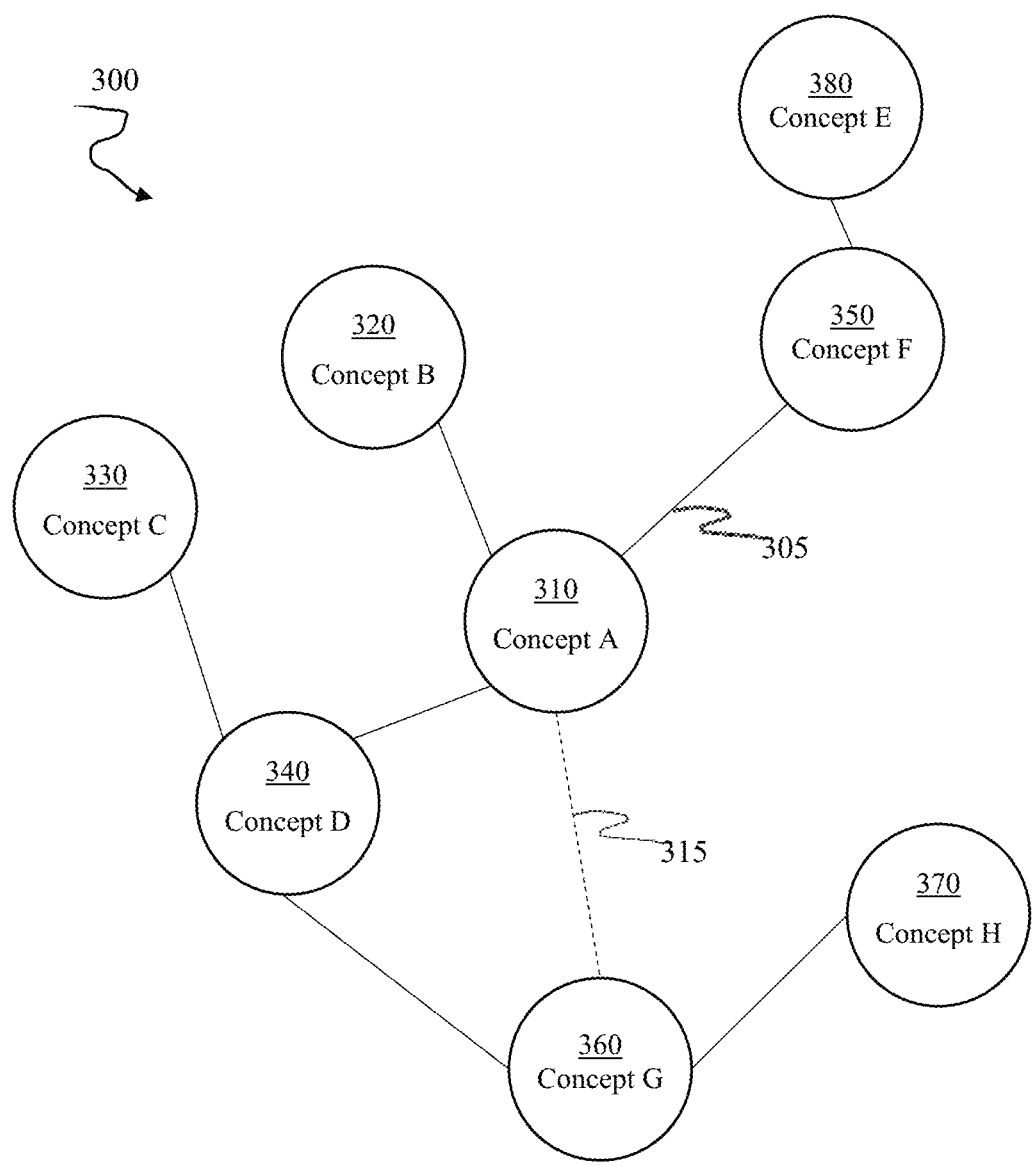
FIG. 3 is a diagram of a Concept Map that can be modeled in the Cognitive Suggestion System (CSS) depicted in FIG. 1.

FIG. 3 is a diagram of a Concept Map that can be modeled in the Cognitive Suggestion System's (CSS), e.g. 130 depicted in FIG. 1 Data Store, e.g. 132 in FIG. 1. A Concept Map can be represented in the Data Store in a variety of ways, but here is depicted as a node-edge graph for ease of discussion. Concepts A, B, C, D, E, F, G, and H are shown along with lines connecting the concepts signifying concept relationships.

The Concept Map consists of nodes associated with concepts and connecting lines or edges that signify relationships between or among the connected concepts. Concepts in the map can be included either through being an Identified Concept, e.g. 134 in FIG. 1, from the participant, e.g. 101A, 101B, in FIG. 1 discussion or by having the Cognitive Suggestion System (CSS), e.g. 130 in FIG. 1, derive additional relevant concepts that are added to the Concept Map and connected by appropriate concept relationships.

Concept Relevance affects what is included by the CSS, e.g. 130 in FIG. 1, via the configuration of more broad or narrow inclusion of concepts already discussed herein possibly actuated by the CSS concept weighting algorithm setting for the system.

When in use by a preferred embodiment, time decay of a concept within a time frame window (already discussed herein) might also affect what concepts are included in the current Concept Map.

Each concept node in the Concept Map is associated with a data record pertaining to that concept. The concept is tagged as to whether it is included in the Concept Map because it is an Identified Concept, e.g. 134 in FIG. 1, or it is a derived concept from the Cognitive Suggestion System (CSS), e.g. 130 in FIG. 1. Concept nodes data records also include a timestamp as to when the concept node was added to the map to be used when considering Concept Relevance using a time decay in a time frame window. Concept node records that are also Identified Concepts include a usage count that is incremented each time the same Identified Concept occurs during the discussion and within the current time frame window when that applies. These Identified Concept counts, as already discussed herein, are used by Relevance Frequency and Relevance Intensity calculations.

A special case of Identified Concept, e.g. 134 in FIG. 1, is a Concept Nexus. Returning to FIG. 3, Concept Nexus is Concept A 310. The Concept Nexus data record count is higher than any other concept node data record counts in the Concept Map. The Concept Nexus is considered, at the particular instance in time reflected in this Concept Map, to be the focal point of the participant, e.g. 101A, 101B in FIG. 1 discussion.

FIG. 3 depicts Concept A being directly related to Concepts B, D, and F. Concept F is directly related to Concept E. Concept D is directly related to Concepts C and G. Concept G is directly related to Concept H.

FIG. 3 lines connecting Concept nodes depict semantic relationships between those connected nodes. Line 305 connecting Concept A 310 Concept F 350 is a solid line, and is representative of all other solid lines shown in FIG. 3, signifying direct semantic relationships between the nodes at each end of the connecting lines. The dashed or dotted line 315 connecting Concept A 310 and Concept G 360 is depicted here to describe other types of concept relationships that may or may not be direct relationships, but that are considered to be important connections to consider in the particular domain or embodiment of the system.

We return to our strawberry example discussed earlier herein. Concept A 310 is strawberries. Concept D 340 is propagation and Concept C 330 is rhizomes. Concept H 360 is climate and Concept G 360 is local weather for agriculture. Concept F 350 is strawberry supply chain and Concept E is trucks. Concept B is pests. We can see by the Concept Map that the participant, e.g. 101A, 101B in FIG. 1, discussion is focused on strawberries and looked at in wider context, strawberry growing for distribution through the supply chain. Weather and pests provide additional information when growing strawberries.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of using biofeedback to facilitate a discussion between at least a first participant and a second participant, comprising:
   using an electronic processing system during the discussion to execute the following steps, in sequence:
   (a) inferring a first concept from words expressed by at least the first participant;
   (b) sourcing, from an electronic data repository external to the discussion, a first content related to the first inferred concept, by expanding terms used by any of the participants in expressing the first inferred concept;
   (c) detecting use by at least one of the participants, of a first trigger expression; and
   (d) using detection of the first trigger expression to render at least some of the first content to at least the first participant as a first electronic biofeedback signal; and
   the electronic processing system further inferring a different second concept from the words expressed by at least the first participant, and weighting the first and second inferred concepts according to relative times that the first and second inferred concepts have been discussed in the discussion.

2. The method of claim 1, further comprising using the second concept to trigger a different second electronic biofeedback signal.

3. The method of claim 2, wherein at least the first participant uses the first electronic biofeedback signal to begin discussion of the different second inferred concept.

4. The method of claim 1, wherein the first trigger expression is a non-question, non-instruction expression.

5. The method of claim 1, further comprising the electronic processing system utilizing profile information of the first participant to assist in sourcing the first content.

6. The method of claim 1, further comprising using an electronic processing system to ask a question to the first participant, and utilizing an answer to the question to assist in sourcing the first content.

7. The method of claim 1, further comprising using an expression characteristic of the first participant to assist in sourcing the first content.

8. The method of claim 1, further comprising using an artificial intelligence (AI) system to assist in sourcing the first content.

9. The method of claim 1, further comprising symantically expanding terms used by the first participant to assist in sourcing the first content.

10. The method of claim 1, further comprising using terms expressed by the first participant to make a $2^{nd}$ order correlation, and using the $2^{nd}$ order correlation to assist in sourcing the first content.

11. The method of claim 1, further comprising rendering the first electronic biofeedback signal to the first participant as a computer-generated graphical image.

12. The method of claim 11, further comprising using an electronic processing system to create the computer-generated graphical image de novo during the discussion.

13. The method of claim 1, further comprising delaying rendering of the first electronic biofeedback signal to the first participant pending a lull in the discussion.

14. The method of claim 1, further comprising utilizing at least a portion of the first inferred concept to create an agenda, and rendering the agenda to the first participant.

15. The method of claim 1, wherein the words from which the first concept is inferred includes a sentence.

* * * * *